United States Patent
Mohr et al.

(10) Patent No.: US 8,029,516 B2
(45) Date of Patent: Oct. 4, 2011

(54) BRACING OF BUNDLED MEDICAL DEVICES FOR SINGLE PORT ENTRY, ROBOTICALLY ASSISTED MEDICAL PROCEDURES

(75) Inventors: Catherine J. Mohr, Mountain View, CA (US); David Q. Larkin, Menlo Park, CA (US); Bruce Schena, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1038 days.

(21) Appl. No.: 11/762,222

(22) Filed: Jun. 13, 2007

(65) Prior Publication Data

US 2007/0283970 A1  Dec. 13, 2007

Related U.S. Application Data

(60) Provisional application No. 60/813,198, filed on Jun. 13, 2006.

(51) Int. Cl.
*A61B 19/00* (2006.01)
(52) U.S. Cl. .................................................. 606/130
(58) Field of Classification Search .................. 606/130, 606/129; 600/201, 204, 210, 227–234, 386; 74/490.01; 700/245
See application file for complete search history.

(56) References Cited

U.S. PATENT DOCUMENTS

| | | | |
|---|---|---|---|
| 5,540,648 A * | 7/1996 | Yoon | 600/114 |
| 5,776,144 A * | 7/1998 | Leysieffer et al. | 606/130 |
| 6,478,028 B1 | 11/2002 | Paolitto et al. | |
| 6,582,420 B2 * | 6/2003 | Castaneda et al. | 606/1 |
| 7,201,754 B2 | 4/2007 | Stewart et al. | |
| 2003/0083553 A1* | 5/2003 | Berg | 600/201 |
| 2003/0216613 A1 | 11/2003 | Suzuki et al. | |
| 2007/0123840 A1 | 5/2007 | Cox | |
| 2007/0197896 A1 | 8/2007 | Moll et al. | |
| 2007/0239138 A1 | 10/2007 | Lawrence | |

OTHER PUBLICATIONS

Vertut, Jean and Philippe Coiffet, *Teleoperation and Robotics: Evolution and Development*, English translation Prentice-Hall, Inc., Inglewood Cliffs, NJ, USA, 1986.

* cited by examiner

*Primary Examiner* — Gary Jackson
*Assistant Examiner* — Katherine Dowe

(57) ABSTRACT

Medical devices robotically manipulated by a medical robotic system for performing a medical procedure on a patient are bundled together as a bundled unit and inserted into the patient through a single entry port. Bracing of the bundled unit at the surgical site so as to be constrained in one or more degrees of freedom of movement may be performed using an anchor secured to an anatomic structure at the surgical site and physically coupled to the bundled unit, or using a tool extending out of a distal end of the bundled unit that extends out to an anatomic structure at the surgical site.

25 Claims, 11 Drawing Sheets

BRACING OF BUNDLED MEDICAL DEVICES FOR SINGLE PORT ENTRY, ROBOTICALLY ASSISTED MEDICAL PROCEDURES

CROSS REFERENCE TO RELATED APPLICATIONS

This application claims priority to U.S. provisional application Ser. No. 60/813,198 filed Jun. 13, 2006, which is incorporated herein by reference.

FIELD OF THE INVENTION

The present invention generally relates to the bracing of surgical tools during the performance of medical procedures using medical robotic systems and in particular, to the bracing of bundled medical devices for single port entry, robotically assisted medical procedures.

BACKGROUND OF THE INVENTION

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

Examples of medical robotic systems include the da Vinci® Surgical System and the da Vinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery.

During the performance of a medical procedure, it may be useful to brace the surgical instruments used in performing the medical procedure and/or an image capturing device used for viewing the medical procedure to either dampen vibration at the medical devices or to restrict or otherwise constrain the medical devices in one or more degrees of freedom of movement relative to an anatomic structure at a surgical site. Without such bracing, precise positioning of the end effectors of the surgical tools relative to the anatomical structure may be difficult to control. For example, external forces may be exerted against the end effectors causing them to move. Also, the target tissue being subjected to a medical procedure may move due to its natural movement, or movement of adjacent organs, or the flow of blood through adjacent veins or arteries.

When performing certain medical procedures, it is advantageous to insert the surgical instruments and the image capturing device as a bundled unit through a single port, such as a natural body orifice or a minimally invasive incision, in the patient. In such a bundled unit, however, mechanical coupling between the bundled components may cause undesirable movement of one component as a result of an external force being exerted against another. Thus, bracing of the entire bundled unit may be advantageous for better relative position control of its individual surgical instruments.

OBJECTS AND SUMMARY OF THE INVENTION

Accordingly, one object of one or more aspects of the present invention is a method for bracing a bundled unit of medical devices using an anatomic structure at a surgical site within a patient so as to constrain at least one degree of freedom of movement of the bundled unit during the performance of a medical procedure using medical devices included in the bundled unit.

This and additional objects are accomplished by the various aspects of the present invention, wherein briefly stated, one aspect is a method for bracing a bundled unit of medical devices used to perform a medical procedure at a surgical site within a patient, comprising: manipulating a tool included in the bundled unit so as to secure an anchor held by the tool to an anatomical structure at the surgical site; and coupling the bundled unit to the secured anchor so as to constrain at least one degree of freedom of movement of the bundled unit during performance of the medical procedure.

Another aspect is a method for bracing a bundled unit of medical devices used to perform a medical procedure at a surgical site within a patient, comprising: manipulating a tool included in the bundled unit to extend out of a distal end of the bundled unit and brace the bundled unit against an anatomic structure at the surgical site so as to constrain at least one degree of freedom of movement of the bundled unit during performance of the medical procedure using medical devices included in the bundled unit.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
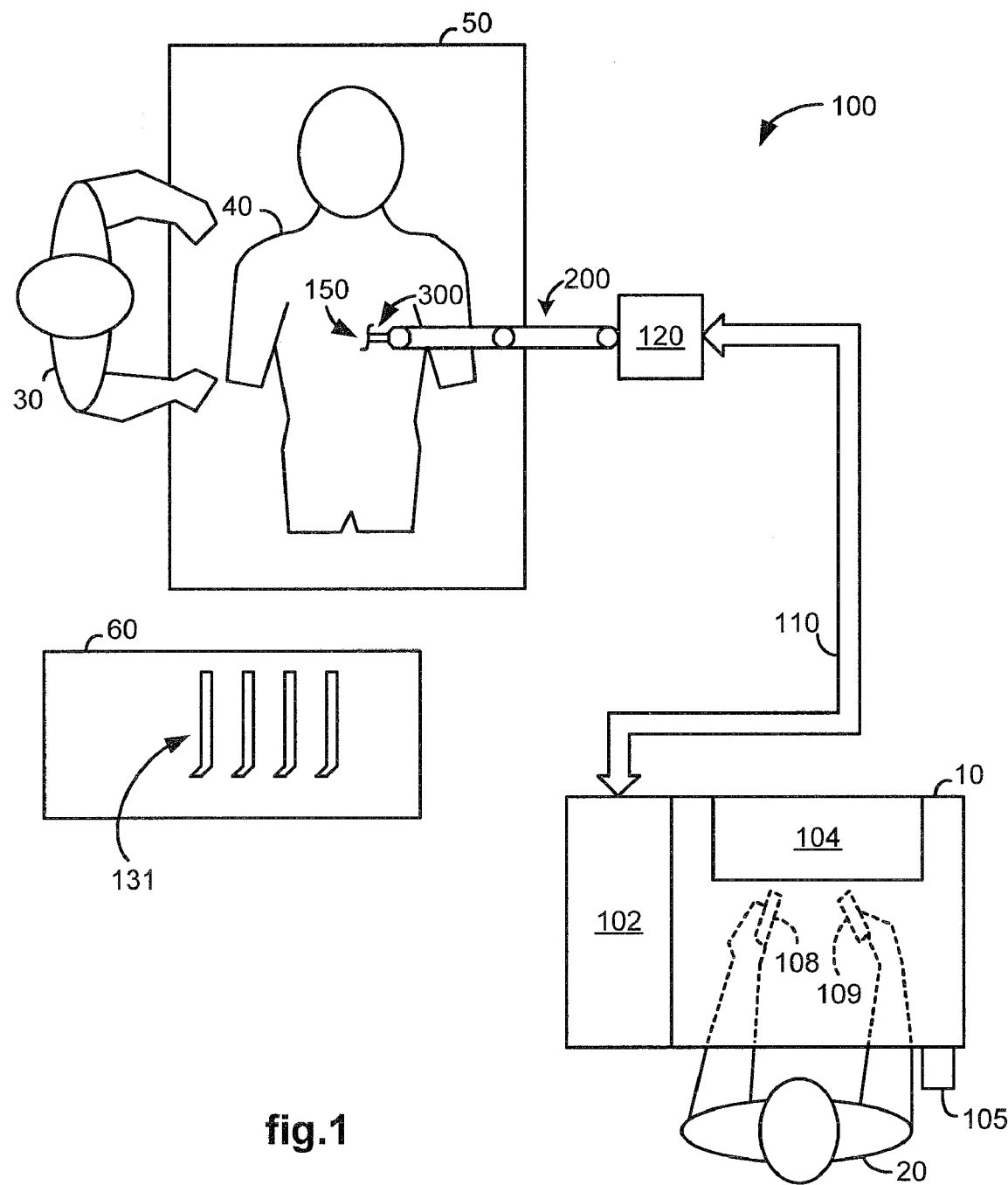
FIG. 1 illustrates a top view of an operating room employing a medical robotic system utilizing aspects of the present invention.

FIG. 1 illustrates, as an example, a top view of an operating room in which a medical robotic system 100 is being utilized by a Surgeon 20 for performing a medical procedure on a Patient 40 who is lying down on an operating table 50. One or more Assistants 30 may be positioned near the Patient 40 to assist in the procedure while the Surgeon 20 performs the procedure teleoperatively by manipulating control devices 108, 109 on a surgeon console 10.

In the present example, a bundled unit 300 of medical devices is inserted through a single entry port 150 into the Patient 40. Although the entry port 150 is a minimally invasive incision in the present example, in the performance of other medical procedures, it may instead be a natural body orifice. The bundled unit 300 is held and manipulated by a robotic arm assembly 200.

The console 10 includes a 3-D monitor 104 for displaying a 3-D image of a surgical site to the Surgeon, left and right manipulatable control devices 108, 109, a foot pedal 105, and a processor 102. The control devices 108, 109 may include any one or more of a variety of input devices such as joysticks, gloves, trigger-guns, hand-operated controllers, or the like. The processor 102 may be a dedicated computer integrated into the console 10 or positioned next or near to it, or it may comprise a number of processing or controller components that are distributed in a distributed processing fashion throughout the system 100.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 3:
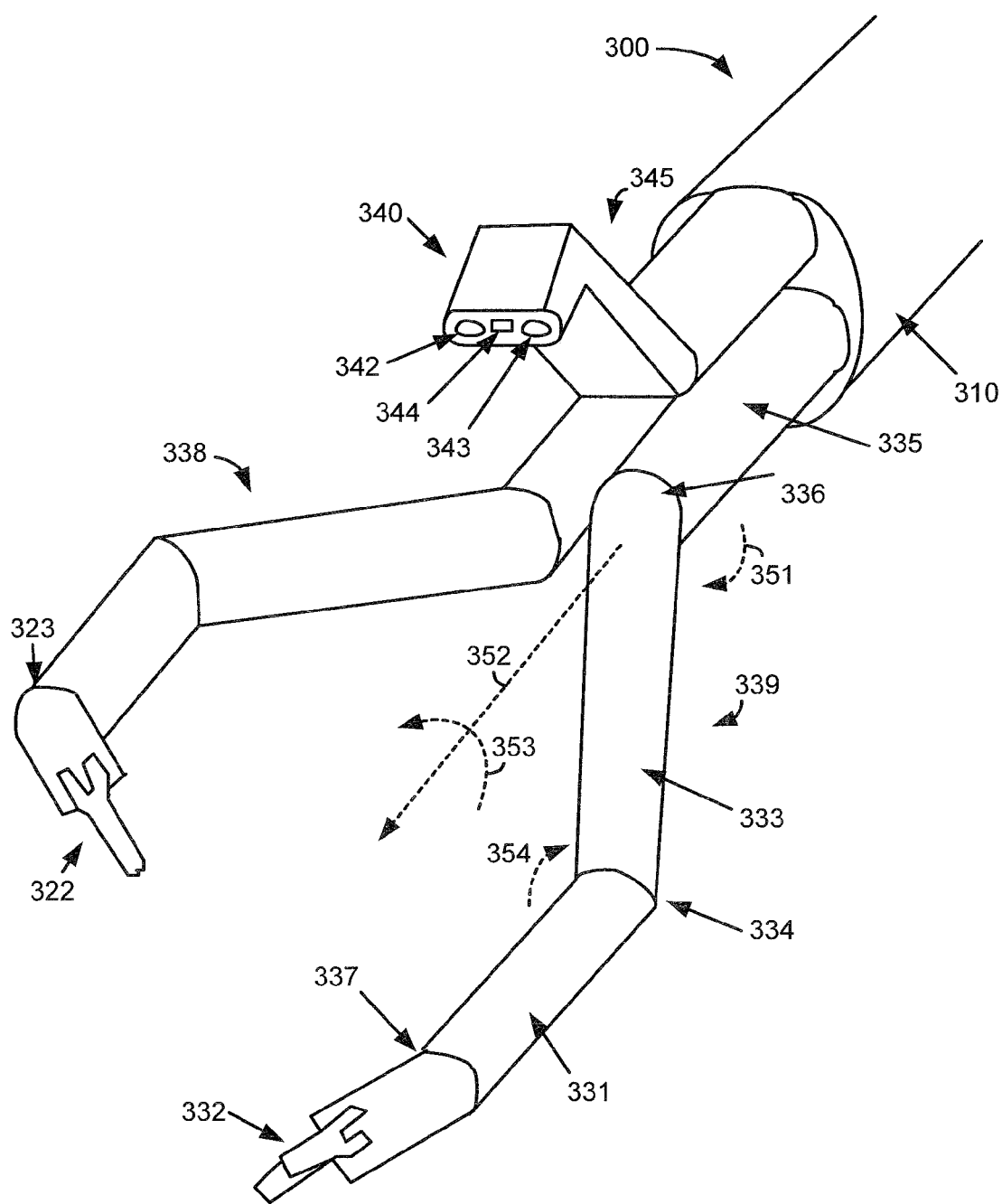
FIG. 3 illustrates a perspective view of a distal end of a bundled unit of medical devices that may be braced at a surgical site by a method utilizing aspects of the present invention.

As shown in FIG. 3, the bundled unit 300 may include two surgical instruments or tools 338, 339 and an image capturing device 340. Each of the surgical tools 338, 339 is associated with one of the control devices 108, 109. The Surgeon performs a medical procedure by manipulating the control devices 108, 109 so that the processor 102 causes corresponding movement of their respectively associated surgical tools 338, 339, while the Surgeon views the surgical site in 3-D on the console monitor 104 as it is captured by the image capturing device 140.

Preferably, control devices 108, 109 will be provided with at least the same degrees of freedom as their associated tools 338, 339 to provide the Surgeon with telepresence, or the perception that the control devices 108, 109 are integral with the tools 338, 339 so that the Surgeon has a strong sense of directly controlling the tools 338, 339.

Preferably, the monitor 104 is positioned near the Surgeon's hands so that it will display a projected image that is oriented so that the Surgeon feels that he or she is actually looking directly down onto the operating site. To that end, images of the tools 338, 339 preferably appear to be located substantially where the Surgeon's hands are located.

In addition, the real-time image is preferably projected into a perspective image such that the Surgeon can manipulate the end effectors 322, 332 of the tools 338, 339 through their corresponding control devices 108, 109 as if viewing the workspace in substantially true presence. By true presence, it is meant that the presentation of an image is a true perspective image simulating the viewpoint of an operator that is physically manipulating the tools 338, 339. Thus, the processor 102 transforms the coordinates of the tools 338, 339 to a perceived position so that the perspective image is the image that one would see if the image capturing device 140 was located directly behind the tools 338, 339.

The processor 102 performs various functions in the system 100. One important function that it performs is to translate and transfer the mechanical motion of control devices 108, 109 to the robotic arm assembly 200 through control signals over bus 110 so that the Surgeon can effectively manipulate the tools 338, 339.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system such as in printed circuit boards installed in the patient side cart 120 and the robotic arm assemblies 128, 129, 200, as well as, or alternatively to, the console 10.

For additional details on the construction and operation of various aspects of a medical robotic system such as described herein, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are incorporated herein by reference.

Figure 2:
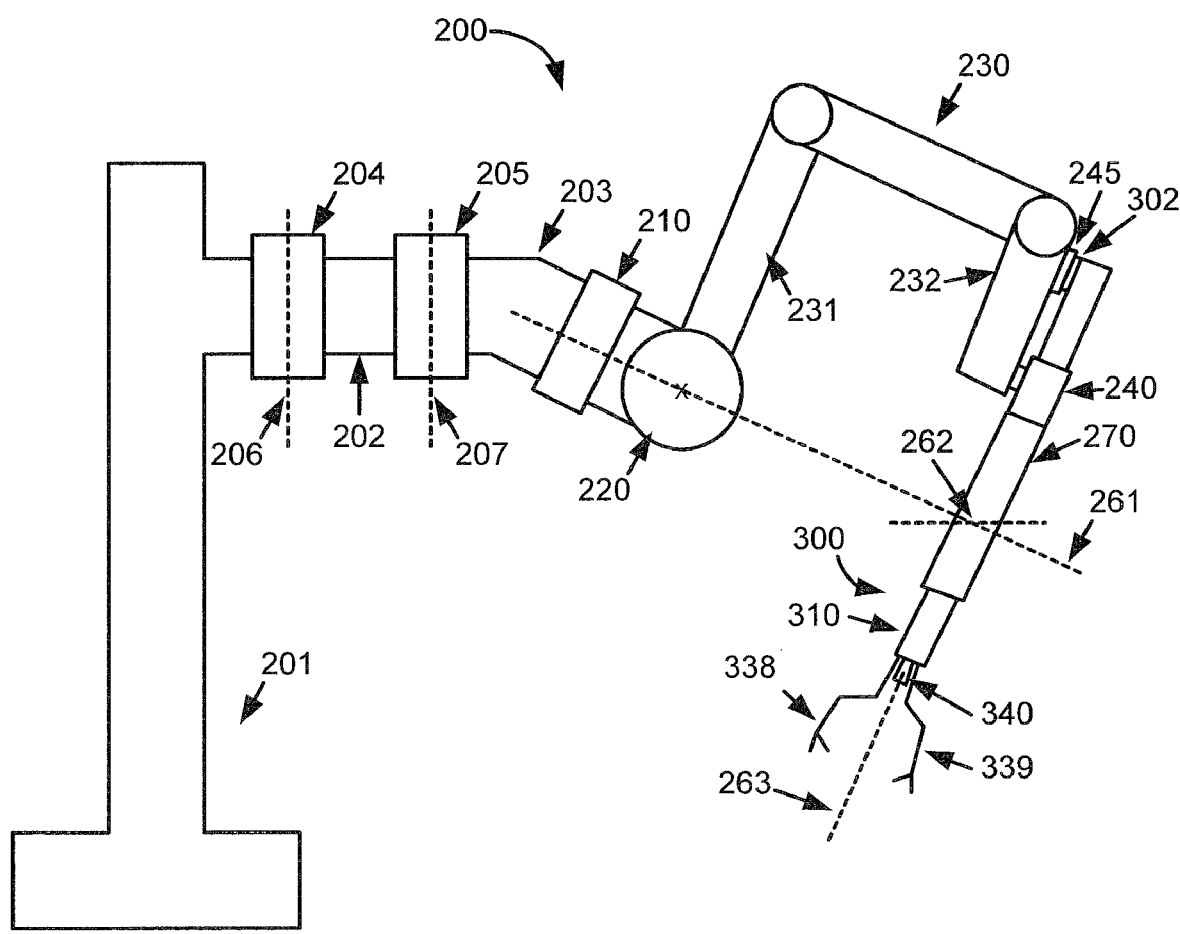
FIG. 2 illustrates a side view of a simplified robotic arm assembly holding a bundled unit of medical devices that may be braced at a surgical site by a method utilizing aspects of the present invention.

FIG. 2 illustrates, as an example, a simplified side view (not necessarily in proportion or complete) of the robotic arm assembly 200 which is holding the bundled unit 300 of medical devices. A tool guide 270 is inserted through the minimally invasive incision 150 in the Patient, and coupled to the robotic arm assembly 200 by a guide holder 240. The bundled unit 300 may then be inserted into the Patient through the tool guide 270. The robotic arm assembly 200 is mechanically supported by a base 201 of the patient side cart 120.

Links 202, 203 are coupled together and to the base 201 through horizontal setup joints 204, 205. The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207.

Although only two links and two setup joints are shown in this example, more or fewer of each may be used as appropriate in this and other robotic arm assemblies in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The robotic arm assembly 200 also includes two active joints and a number of gears driven by motors. A yaw joint 210 allows arm section 230 to rotate around an axis 261, and a pitch joint 220 allows arm section 230 to rotate about an axis perpendicular to that of axis 261 and orthogonal to the plane of the drawing. An interface 302 comprises mating parts on the carriage 245 and the proximal end of the bundled unit 300 such as motor driven gears that actuate movement of the surgical tools 338, 339 and image capturing unit 340 through conventional joints, cable and pulley systems.

The arm section 230 is configured so that sections 231, 232 are always parallel to each other as the pitch joint 220 is rotated by its motor. As a consequence, the bundled unit 300 may be controllably moved by driving the yaw and pitch motors so as to pivot about the pivot point 262, which is generally located through manual positioning of the setup joints 204, 205 so as to be at the point of entry into the Patient. In addition, the bundled unit 300 is coupled to a carriage 245 on the arm section 230 which in turn is coupled to a linear drive mechanism to extend or retract the bundled unit 300 along its insertion axis 263.

Although each of the yaw joint 210, pitch joint 220 and motor driven gears in the carriage 245 is controlled by an individual joint or gear controller, the controllers may be controlled by a common master/slave control system so that the medical devices of the bundled unit 300 may be controlled through user (e.g., Surgeon or operator) manipulation of its associated control device.

FIG. 3 illustrates, as an example, a perspective view of a distal end of the bundled unit 300. The bundled unit 300 includes removable surgical tools 338, 339 for performing a medical procedure and a removable image capturing unit 340 for viewing the procedure at a surgical site within a patient. Each of the tools 338, 339 and image capturing unit 340 extends through a separate lumen formed in an inner core of the bundled unit 300. Replacement of one or both of the surgical tools 338, 339 during or in preparation for performing a medical procedure may then be accomplished by the Assistant removing the tool that is no longer needed from its lumen and replacing it with a substitute tool 131 from a tray 60 by inserting the substitute tool 131 in the vacated lumen. Alternatively, if unused lumens are available, an additional tool may be inserted through one of those available lumens without removing any other tools already in place.

The image capturing unit 340 preferably includes a stereoscopic pair of cameras 342, 343 for three-dimensional imaging of the surgical site and an illuminating device 344 such as a light emitting diode (LED) or a fiber optics bundle carrying light from an external source, to enhance visibility of objects in the captured images. Auxiliary image capturing units, such as an ultrasound probe, may also be provided in available lumens of the bundled unit 300 for "seeing" into anatomic structures for surgical or diagnostic purposes.

In some embodiments, an overtube 310 is also included in the bundled unit 300 for protecting its inner core and the medical devices (i.e., surgical tools and image capturing units) inserted therethrough. The overtube 310 may be rigid. Alternatively, it may be formed of flexible material or comprise actively and/or passively bendable sections so that the bundled unit 300 may conform to the shapes of body lumens as it moves therethrough to a surgical site within a patient.

The surgical tools 338, 339 each have a controllably extendable, rotatable, and bendable arm to which their respective end effectors 322, 332 are coupled to by wrist mechanisms 323, 337. For example, the arm of the surgical tool 339 comprises three links 331, 333, 335 coupled by distal joints 334, 336. The proximal link 335 is controllably extendable and retractable along an insertion axis 352 (which is preferably parallel to the insertion axis 263 of the single-port device 300), and is controllably rotatable (as shown by rotation angle 353) about the insertion axis 352. The middle link 333, on the other hand, is controllably bendable by distal joint 336 relative to the link 335 (as shown by bend angle 351), and the distal link 331 is coupled to the links 333, 335 and bendable by distal joint 334 so that its bend angle 354 is in an opposite direction as that of the link 333 and consequently, keeps links 331, 335 in parallel alignment.

The arm of the surgical tool 338 is similarly constructed as that of the surgical tool 339. Additional details for one example of the wrist mechanisms 323, 337 are provided in commonly owned U.S. Pat. No. 6,817,974 "Surgical Tool Having Positively Positionable Tendon-Actuated Multi-Disk Wrist Joint," which is incorporated herein by this reference.

The image capturing unit 340 also has a controllably extendable, rotatable, and bendable arm 345 that facilitates at least insertion/retraction of the image capturing unit 340 along its insertion axis (which may be parallel to the insertion axis 263 of the single-port device 300) and pitch motion in order to achieve a sufficient elevation of the image capturing device 340 "above" the surgical tools 338, 339 so as to properly view them during a surgical procedure. Additional degrees of freedom, such as roll angular movement of the image capturing device 340 about its insertion axis, may also be provided in order to facilitate additional positioning and orientation capabilities for the image capturing device 340. For enhanced maneuverability, the image capturing arm 345 may also be bendable such as the controllably bendable, rotatable, and extendable arms of the surgical tools 338, 339.

Figure 4:
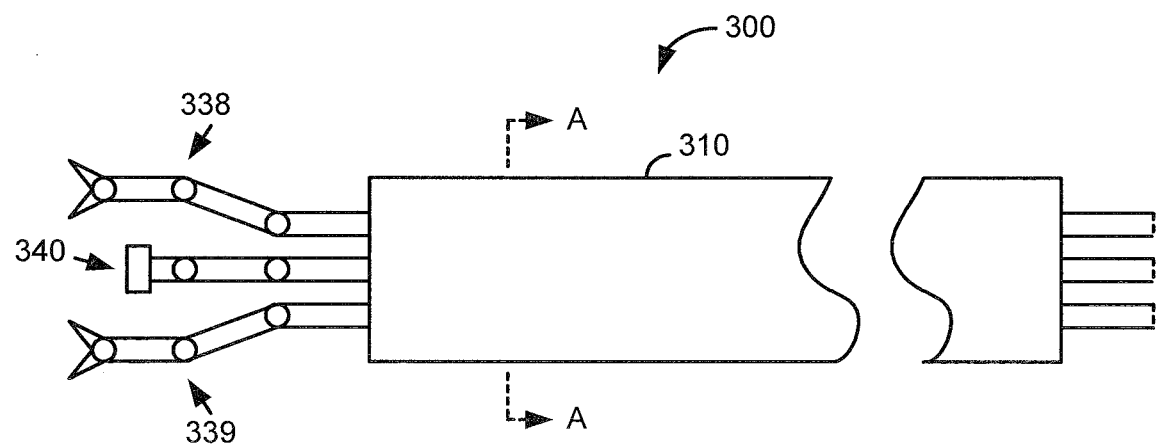
FIGS. 4~5 illustrate simplified top and cross-sectional views of a bundled unit of medical devices that may be braced at a surgical site by a method utilizing aspects of the present invention.
Figure 5:
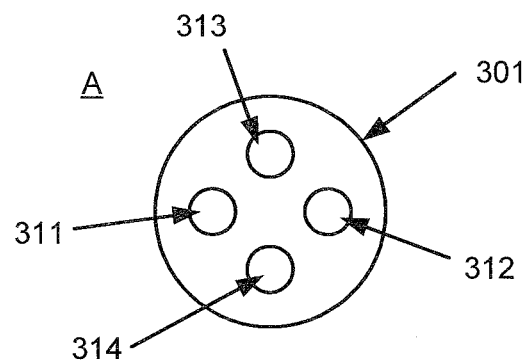

FIGS. 4-5 illustrate top and cross-sectional views of the bundled unit 300. The bundled unit 300 includes an overtube 310 which has a plurality of lumens 311~314 extending between its distal and proximal ends. In an exemplary configuration, a pair of surgical tools 338, 339 are inserted in lumens 311, 312, and an image capturing device 340 inserted in lumen 313. Lumen 314 is available for insertion of another medical device such as an auxiliary image capturing device or a tool such as one that may be used for bracing the bundled unit 300 at a surgical site within the Patient.

Figure 6:
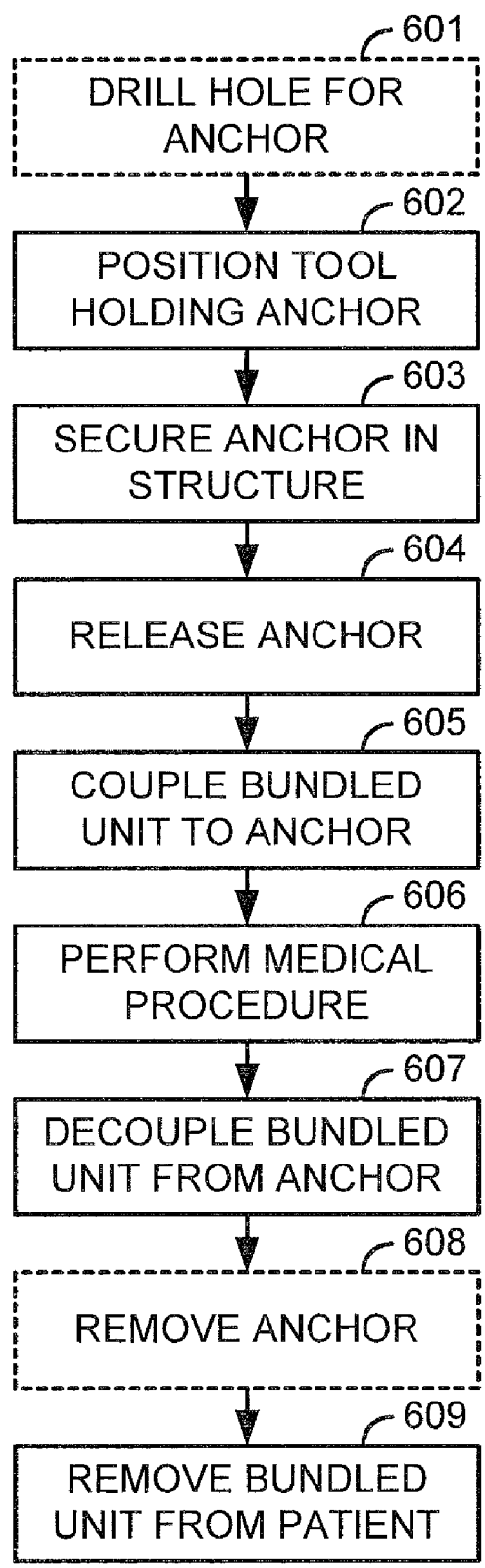
FIG. 6 illustrates a flow diagram of a method for bracing a bundled unit of medical devices used to perform a medical procedure at a surgical site within a patient, utilizing aspects of the present invention.
Figure 7:
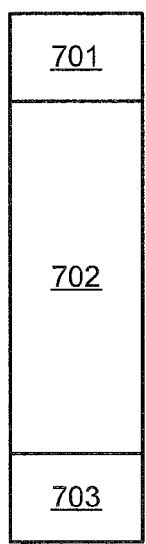
FIG. 7 illustrates a generic anchor used in a method for bracing a bundled unit of medical devices at a surgical site within a patient, utilizing aspects of the present invention.

FIG. 6 illustrates, as an example, a flow diagram of a method for constraining the bundled unit 300 in at least one degree of freedom movement relative to an anatomic structure (e.g., bone, muscle, tendon, tissue, etc.) at a surgical site within the Patient using an anchor secured to the anatomic structure while performing a medical procedure at the surgical site, and FIG. 7 illustrates, as an example, a generic form of an anchor 700 which may be used with the method. The method in this case is generally performed by the Surgeon as he or she operates the control devices 108, 109 of the medical robotic system 100 so as to teleoperatively manipulate associated tools in the bundled unit 300.

Figures 8, 9:
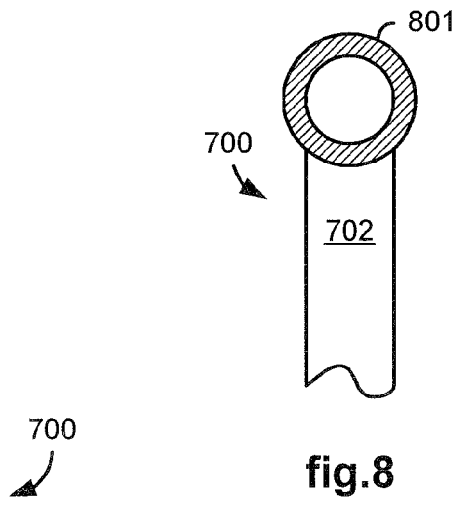
FIGS. 8~9 illustrate simplified side views of examples of anchor coupling elements used with a method utilizing aspects of the present invention.
Figure 10:
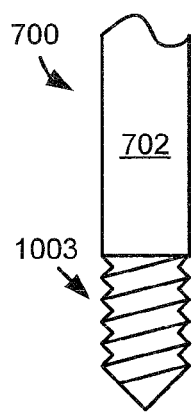
FIGS. 10~11 illustrate simplified side views of examples of anchor attaching elements used with a method utilizing aspects of the present invention.
Figure 11:
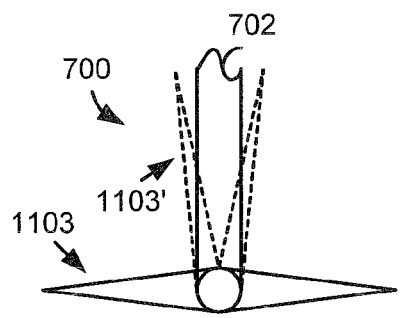

As shown in FIG. 7, the anchor 700 comprises three primary parts, a coupling element 701 which facilitates coupling the bundled unit 300 to the anchor 700, a post or extension element 702, and an attaching element 703 which facilitates securing the anchor 700 to the anatomic structure. FIGS. 8~9 illustrate, as examples, various embodiments of the coupling element 701 that may be incorporated into the anchor 700, and FIGS. 10~11 illustrate, as examples, various embodiments of the attaching element 703 that may be incorporated into the anchor 700.

As shown in 601 of FIG. 6, the method may start by robotically manipulating a tool to drill a hole into the anatomic structure to facilitate securing the anchor to the anatomic structure. For example, if the anchor 700 is a T-bar such as shown in FIG. 11, a hole of appropriate size may be drilled in the anatomic structure so that wings of the T-bar may fit through the hole in their retracted position 1103' and subsequently secure the anchor to the anatomic structure when placed in their extended position 1103. On the other hand, if the anchor has an attaching element 703 such as the screw 1003 shown in FIG. 10, then it may not be necessary to drill the hole since the attaching element may be screwed directly into the anatomic structure, thereby making 601 unnecessary. Accordingly, 601 may considered an optional procedure that depends upon the type of attaching element 703 that is incorporated on the anchor 700. Drilling may also be unnecessary if the anchor 700 is a T-bar such as shown in FIG. 11, if the T-bar is configured with a tip that can pierce the anatomic structure.

Figure 12:
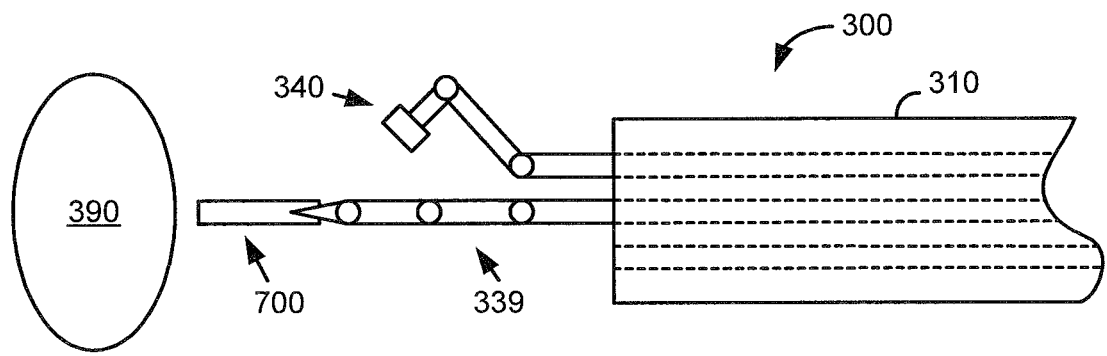
FIG. 12 illustrates a simplified side view of bundled unit of medical devices at a surgical site with a tool in the bundled unit preparing to secure an anchor into a target tissue as part of a method utilizing aspects of the present invention.
Figure 13:
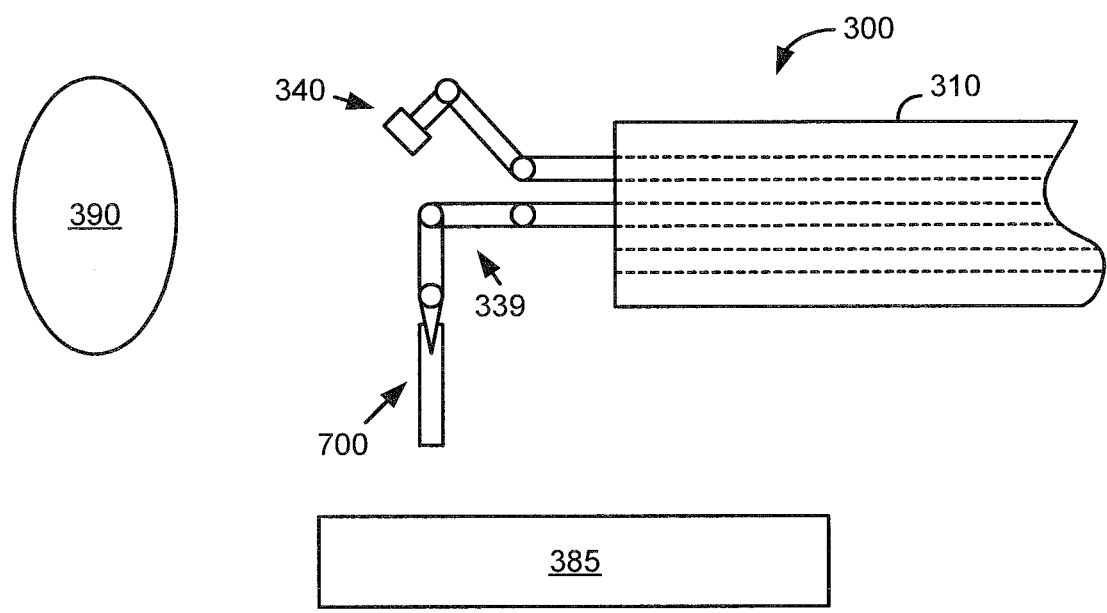
FIG. 13 illustrates a simplified side view of bundled unit of medical devices at a surgical site with a tool in the bundled unit preparing to secure an anchor into an anatomic structure adjacent a target tissue as part of a method utilizing aspects of the present invention.

In 602, the method proceeds by robotically manipulating a tool holding the anchor to be positioned where it may subsequently secure the anchor to the anatomic structure at the surgical site. As one example, FIG. 12 shows the surgical tool 339 holding the anchor 700 (by grasping it with its end effector 332) and being robotically positioned to secure it to an anatomic structure that is the target tissue 390. The tissue is referred to as being the target tissue, because it is tissue that is being targeted as part of the medical procedure. As another example, FIG. 13 shows the surgical tool 330 holding the anchor 700 and being robotically positioned to secure it to an anatomic structure 385, which is sufficiently close to the target tissue 390 that the surgical tools of the bundled unit 300 may perform the medical procedure when the bundled unit 300 is coupled to the secured anchor 700.

In 603, the method proceeds by robotically manipulating the tool holding the anchor so that it secures the anchor to the anatomic structure. The specific procedure used to secure the anchor 700 depends upon the type of its attaching element 703. For example, if the attaching element 703 is the screw 1003 shown in FIG. 10, then the tool may simply screw the anchor 700 into the anatomic structure in the same fashion as a screw driver would be used. On the other hand, if the attaching element 703 is a needle (not shown), it may simply be pushed into the anatomic structure. As can be readily appreciated, the needle may be a suitable attaching element 703 when the anatomic structure to be secured to is soft tissue, and the screw may be a suitable attaching element 703 when the anatomic structure to be secured to is a bone. As still another example, if the attaching element 703 of the anchor 700 is a T-bar, then it may be secured to the anatomic structure by first inserting the wings of the T-bar in their retracted position through a pre-drilled hole in the anatomic structure, then causing the wings to be positioned in their expanded position after they have been inserted through the hole (and presumably through the anatomic structure to an opening), and finally, securing the wings in their expanded positions.

In 604, the method proceeds by robotically manipulating the tool to release its hold on the anchor, and in 605, by robotically manipulating the bundled unit 300 (or one of its bundled medical devices) to be physically coupled to the secured anchor 700. The specific procedure used to couple the bundled unit 300 to the anchor 700 depends upon the type of coupling element 701 configured on the anchor 700.

Figure 14:
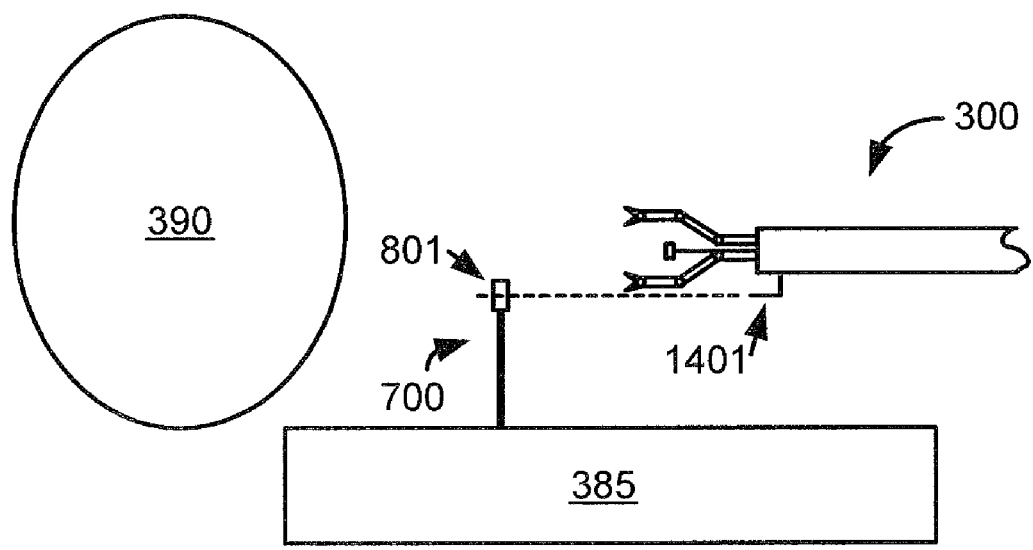
FIGS. 14~15 illustrate simplified top views of a surgical site before and after coupling a bundled unit of medical devices to an anchor that has been secured to an anatomic structure for bracing the bundled unit against the anatomic structure, utilizing aspects of the present invention.
Figure 15:
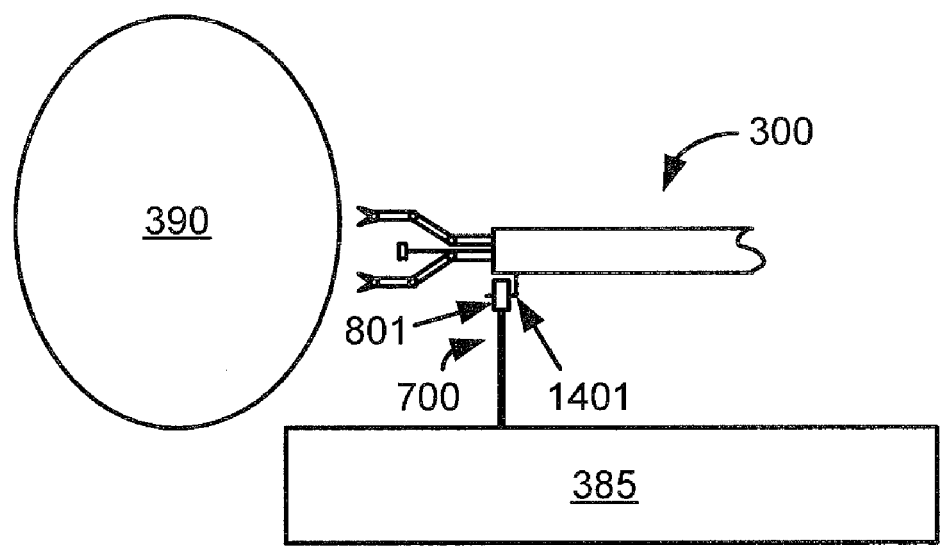

For example, if the coupling element is the eyelet 801 shown in FIG. 8, then a corresponding male member of the bundled unit 300 is inserted into the eyelet 801 to couple the two together. In particular, as shown in FIGS. 14~15, a male member 1401 on the overtube 310 of the bundled unit 300 is first lined up for insertion into eyelet 801, and then inserted in the eyelet 801 to couple the bundled unit 300 to the anchor 700. The shape of the male member 1401 is in the form of a hook in this case so that forward movement of the bundled unit 300 is constrained when the male member 1401 is inserted in the eyelet 801.

Figure 16:
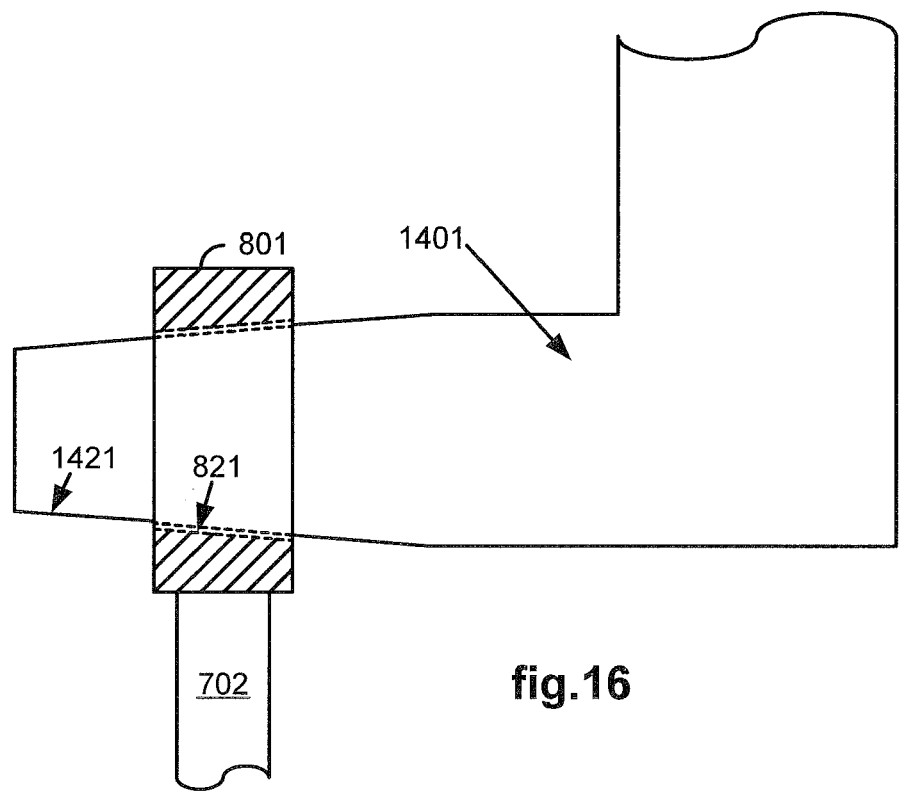
FIGS. 16~17 illustrate simplified partial side views of two different anchor coupling element embodiments providing different degree of freedom of motion constraints to their respectively coupled bundled units, utilizing aspects of the present invention.
Figure 17:
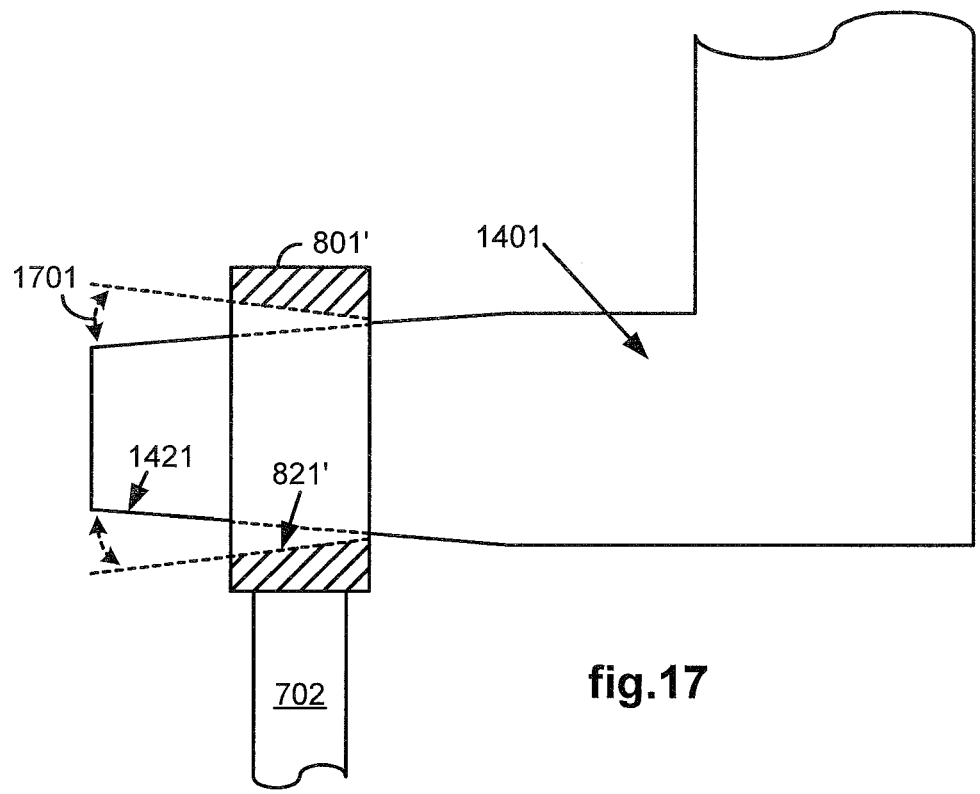

Additional degrees of freedom of movement may also be constrained depending upon the shapes and tapers of the eyelet and the mating male member. For example, the round shape of the eyelet 801 allows the male member 1401 to rotate in the eyelet 801 and consequently, the bundled unit 300 to rotate about the insertion axis of the male member 1401 into the eyelet 801. A square or other edged eyelet shape, however, would constrain such rotation. As another example, if the upper and lower inner walls 821 of the eyelet 801 and the corresponding outer edges 1421 of the male member 1401 are tapered in the same direction as shown in FIG. 16, then the male member 1401 is constrained from rotating in a pitch direction. However, if the upper and lower inner walls 821' of the eyelet 801' and the corresponding outer edges 1421 of the male member 1401 are tapered in opposite directions such as shown in FIG. 17, then the male member 1401 is allowed some pitch movement as shown by arrow 1701. Tapering directions of the side walls of the eyelet 801 may similarly allow or constrain the male member 1401 from rotating in a yaw direction.

Although the male member is shown in FIGS. 14~15 as being formed on the overtube 310, a tool extending out of the distal end of the bundled unit 300 may also be used to hook into the eyelet 801 of the anchor 700. The tool in this case may be a controllably extendable and bendable three-link arm that is inserted through the spare lumen 314 of the core of the bundled unit 300 and robotically controlled like the extendable arms of the surgical tools 338, 339 to bend the three-link arm so that a distal link of the arm may be hooked into the eyelet 801.

Figure 18:
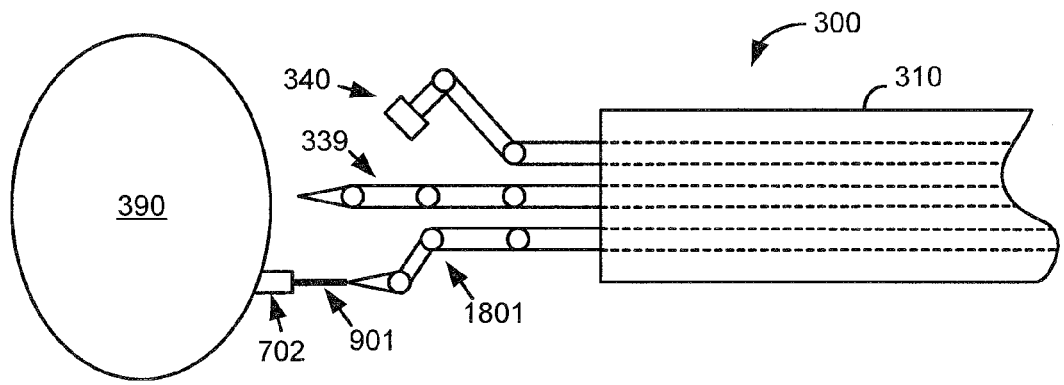
FIG. 18 illustrates a simplified side view of a bundled unit of medical devices being braced by one of the medical devices pulling on a tether coupling element of a secured anchor according to a method utilizing aspects of the present invention.

As another example of securing the bundled unit 300 to the secured anchor 700, if the coupling element of the anchor 700 is the tether 901 shown in FIG. 9, then a spare surgical instrument 1801 having a gripper-type end effector (e.g., an end effector configured with pliers-like jaws) may be inserted in the spare lumen 314 and controlled to grip and hold the tether 901 as shown in FIG. 18. In this way, the bundled unit 300 is constrained from moving away from the secured anchor 700 any farther than the length of the tether 901.

As another example of securing the bundled unit 300 to the secured anchor 700, if the coupling element 701 of the anchor 700 is a material that is attracted to a magnet, then a tool having an electromagnetic (or otherwise magnetized) tip may be inserted in the spare lumen 314 or an electromagnetic (or otherwise magnetized) element may be disposed on the overtube 310 of the bundled unit 300 (such as the male member 1401 shown in FIG. 14). To secure the bundled unit 300 to the secured anchor 700, the electromagnetic tip or element may then be energized when it is sufficiently close to or in physical contact with the coupling element 701. Releasing the bundled unit 300 from the secured anchor 700 is then a simple matter of de-energizing the electromagnetic tip or element. Energizing and de-energizing of the electromagnetic tip or element is preferably controlled in this case by an input manipulated by the Surgeon at the Surgeon's console 10, such as the foot pedal 105 or a button on one of the control devices 108, 109.

In 606, once the bundled unit 300 is coupled to the secure anchor 700 and consequently, braced (i.e., constrained in one or more degrees of freedom of movement), the end effectors 322, 332 of the surgical tools 338, 339 (and other surgical instruments or tools that may be substituted for them) may be robotically manipulated by the Surgeon to perform a medical procedure on the target tissue 390 with the image capturing unit 340 positioned so as to allow the Surgeon to view the surgical site in real-time on the console monitor 104. After completion of the medical procedure, in 607, the method proceeds by robotically manipulating the bundled unit 300 so as to decouple it from the anchor 700 by, for example, robotically removing a male member of the bundled unit 300 from an eyelet of the secured anchor 700, robotically releasing a tether of the anchor 700, or de-energizing an electromagnetic tip or element that is in physical contact with the coupling element 701 of the secured anchor 700, depending upon the type of coupling element used on the anchor 700.

In 608, the secured anchor 700 may optionally be removed from the anatomic structure that it is secured to by, for example, either unscrewing it or releasing the wings of a T-bar so that it releases its hold on the anatomic structure, depending upon the type of attaching element used on the anchor 700. Alternatively, if the anatomic structure is to be removed as part of the medical procedure, then the anchor 700 may remain secured to the anatomic structure so that it is removed along with the anatomic structure.

Finally, in 609, the bundled unit 300 may be removed from the Patient by robotically retracting it back to its port of entry. If the anatomic structure is to be removed, an end effector of one of the surgical tools 338, 339 may grip the anatomic structure (after it has been severed, if necessary) so that it is pulled out with the bundled unit 300.

Figure 19:
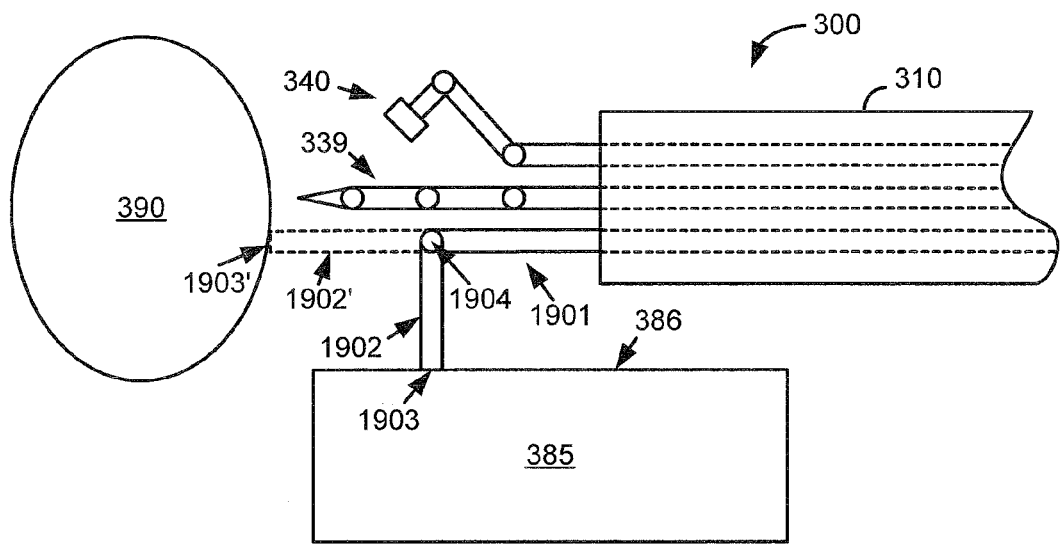
FIG. 19 illustrates a simplified side view of a bundled unit of medical devices being braced by a tool extending out of a distal end of the bundled unit against an anatomic structure according to a method utilizing aspects of the present invention.

As shown in FIG. 19, bracing of the bundled unit 300 may also be performed by merely applying point pressure against an anatomic structure 385 instead of coupling to a secured anchor. Such a technique, however, constrains movement of the bundled unit 300 in only the translational direction of the anatomic structure, so that the anatomic structure effectively acts as a wall that the bundled unit 300 cannot pass through. The point pressure may be applied by an extendable and bendable arm 1901 that is inserted through spare lumen 314 and robotically controlled like the extendable, rotatable and bendable arms of surgical instruments 338, 339. A distal link 1902 (shown using solid lines) of the arm 1901 may be bent at joint 1904 so that its distal end 1903 provides point pressure against an anatomic structure 385, or the distal link 1902' (shown using dotted lines) may be unbent at joint 1904 so that its distal end 1903' provides point pressure against the target tissue 390. Note that if the anatomic structure or target tissue to which the point pressure is being applied, is to be removed as part of the medical procedure, the distal end 1903 may be configured with an attaching element (such as a screw or T-bar) so that the anatomic structure or target tissue, as the case may be, may be withdrawn along with the bundled unit 300 at the completion of the medical procedure.

Figure 20:
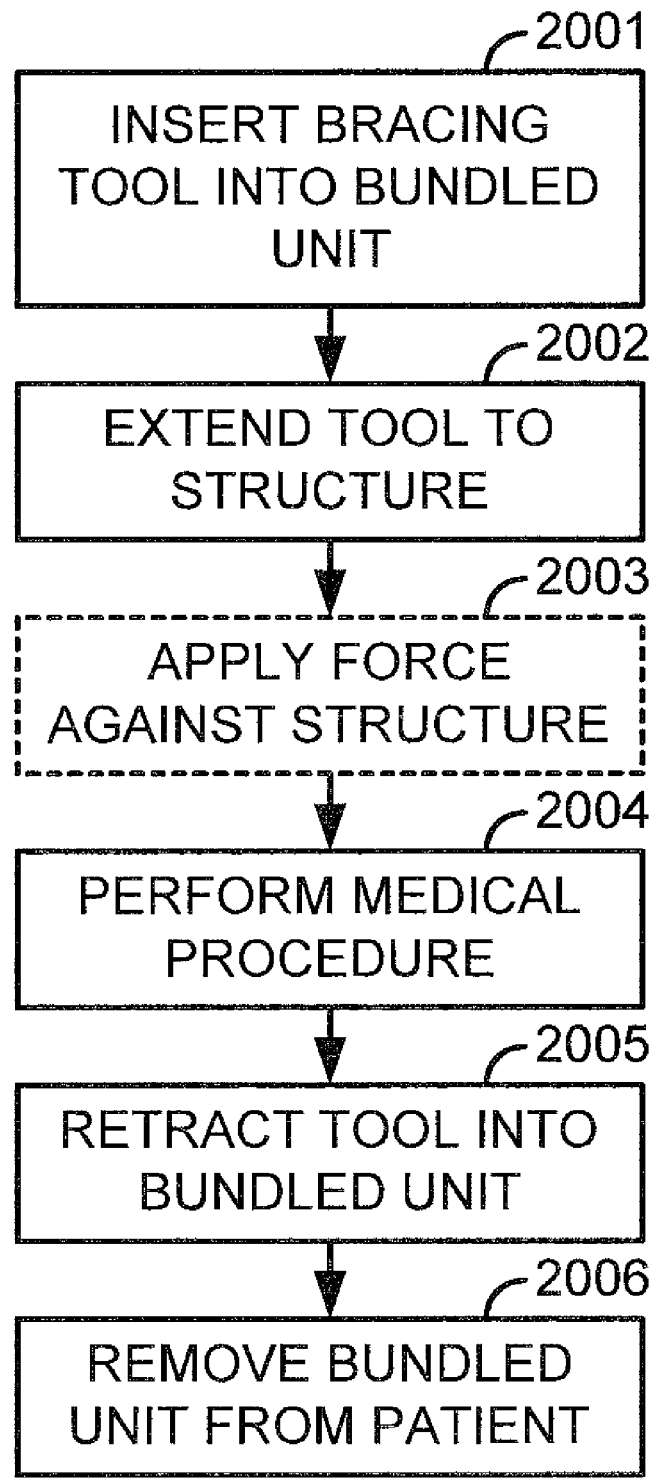
FIG. 20 illustrates a flow diagram of an alternative method for bracing a bundled unit of medical devices used to perform a medical procedure at a surgical site within a patient, utilizing aspects of the present invention.

FIG. 20 illustrates, as an example, an alternative method for bracing a bundled unit of medical devices used to perform a medical procedure at a surgical site within the Patient, using the extendable and bendable arm 1901 (also referred to herein as the "bracing tool") shown and described in reference to FIG. 19.

In 2001, the bracing tool 1901 is inserted through an available lumen of the bundled unit 300. In 2002, the method proceeds by robotically manipulating the tool 1901 so that its distal link extends to anatomic structure at the surgical site. The anatomic structure in this case may be the target tissue 390, which is to be treated during the medical procedure, or an anatomic structure 385 that is proximate to the target tissue 390. In 2003, a force may optionally be applied in the direction of the anatomic structure so that if the anatomic structure moves away from the point pressure, the distal link and consequently, the bundled unit 300 will follow it. In 2004, the medical procedure is then performed by the Surgeon robotically manipulating the medical devices of the bundled unit 300. After the medical procedure is completed, in 2005, the bracing tool 1401 is robotically manipulated so as to be retracted back towards the distal end of the bundled unit 300, and in 2006, the bundled unit 300 is removed from the patient.

In the above description, manipulation of tools other than the surgical tools 338, 339 that are used to perform the medical procedure is occasionally required. If one of the control devices 180, 109 is required to control the Surgeon's manipulation of one of these non-surgical tools, then it may be necessary to temporarily switch association of the control device to the non-surgical tool. Once Surgeon manipulation of the non-surgical tool is completed, then the control device may be associated back to its originally associated surgical tool. At that point in time, the non-surgical tool may be fixed in its position, such as being coupled to a secured anchor, grasping a tether, or being extended against an anatomical structure for bracing against the structure. Such switching of tool associations may be performed in a similar manner as that conventionally employed for sharing control devices between an image capturing device and the surgical tools.

Although the various aspects of the present invention have been described with respect to a preferred embodiment, it will be understood that the invention is entitled to full protection within the full scope of the appended claims.

We claim:

1. A method for bracing a bundled unit of medical devices used to perform a medical procedure at a surgical site within a patient, comprising:
   manipulating a tool included in the bundled unit so as to secure an anchor held by the tool to an anatomical structure at the surgical site; and
   coupling the bundled unit to the secured anchor so as to constrain at least one degree of freedom of movement of the bundled unit during performance of the medical procedure.

2. The method according to claim 1, wherein the medical procedure is to be performed on a target tissue at the surgical site, and the anatomical structure is adjacent to the target tissue.

3. The method according to claim 1, wherein the medical procedure is to be performed on a target tissue at the surgical site, and the anatomical structure is the target tissue.

4. The method according to claim 1, wherein the anchor comprises a coupling element for coupling the anchor to the bundled unit, and an attaching element for securing the anchor to the anatomical structure.

5. The method according to claim 4, wherein the coupling element is an eyelet.

6. The method according to claim 5, wherein the coupling of the bundled unit to the secured anchor comprises: inserting a male member of the bundled unit into the eyelet of the anchor.

7. The method according to claim 6, wherein the eyelet and the male member are shaped so as to constrain at least one rotational movement of the male member when inserted in the eyelet.

8. The method according to claim 6, wherein the inner wall of the eyelet and the outer surface of the male member are configured so as to constrain at least one rotational movement of the male member when inserted in the eyelet.

9. The method according to claim 6, wherein the male member is controllably extendable out of a distal end of the bundled unit.

10. The method according to claim 6, wherein the male member is a hook structure attached to an outer surface of the bundled unit.

11. The method according to claim 4, wherein the coupling element is a tether.

12. The method according to claim 11, wherein the robotic coupling of the bundled unit to the secured anchor comprises: manipulating a tool in the bundled unit so as to grasp the tether.

13. The method according to claim 4, wherein the coupling element is a material characterized by being attracted to a magnet.

14. The method according to claim 13, wherein the robotic coupling of the bundled unit to the secured anchor comprises: energizing an electromagnetic tip of a tool inserted in the bundled unit so as to magnetically attract the coupling element.

15. The method according to claim 13, wherein the robotic coupling of the bundled unit to the secured anchor comprises: energizing an electromagnetic element disposed on the bundled unit so as to magnetically attract the coupling element.

16. The method according to claim 4, wherein the attaching element is a screw.

17. The method according to claim 16, wherein the manipulating of the tool included in the bundled unit so as to secure an anchor held by the tool to the anatomical structure at the surgical site, comprises: manipulating the tool so that it rotates and exerts a force against the screw sufficient to screw the screw into the anatomic structure.

18. The method according to claim 4, wherein the attaching element includes retractable and expandable wings.

19. The method according to claim 18, further comprising:
manipulating a drill included in the bundled unit so as to drill a hole in the anatomic structure where the anchor be secured;
wherein the manipulation of the tool used to secure the anchor held by the tool to the anatomical structure at the surgical site comprises inserting the wings of the attaching element in their retracted position into the hole, causing the wings to be placed in their expanded position after exiting the hole on an opposite of entry, and securing the wings in their expanded position so as to secure the anchor to the anatomic structure.

20. The method according to claim 1, further comprising prior to manipulating the tool:
inserting the bundled unit through a port into the patient.

21. The method according to claim 20, wherein the port is a minimally invasive incision and the medical procedure is a minimally invasive surgical procedure.

22. The method according to claim 20, wherein the port is a natural body orifice.

23. The method according to claim 1, wherein the bundled unit comprises at least one tool for performing the medical procedure and an image capturing device for viewing the medical procedure at the surgical site.

24. The method according to claim 1, wherein the manipulation of the tool comprises:
robotically manipulating the tool so as to secure the anchor held by the tool to the anatomical structure.

25. The method according to claim 1, wherein the coupling of the bundled unit to the secured anchor comprises:
robotically coupling the bundled unit to the secured anchor so as to constrain at least one degree of freedom of movement of the bundled unit during performance of the medical procedure.

* * * * *